United States Patent [19]

Sekiya

[11] Patent Number: 4,462,802
[45] Date of Patent: Jul. 31, 1984

[54] DENTAL ROOT MARKING AND MEASURING INSTRUMENT FOR ENDODONTIC SURGERY

[76] Inventor: Akio Sekiya, 12-32, Sakae 3-chome, Naka-ku, Nagoya-shi, Aichi-ken, Japan

[21] Appl. No.: 457,685

[22] Filed: Jan. 13, 1983

[51] Int. Cl.³ .............................................. A61C 19/04
[52] U.S. Cl. .................................... 433/72; 433/102; 433/224
[58] Field of Search ..................... 433/72, 102, 224, 81

[56] References Cited

U.S. PATENT DOCUMENTS 2,436,623  2/1948  Van Zile .............................. 433/81
3,916,529  11/1975  Moussezu ........................... 433/224

*Primary Examiner*—Robert Peshock
*Attorney, Agent, or Firm*—Armstrong, Nikaido, Marmelstein & Kubovcik

[57] ABSTRACT

A dental root marking and measuring instrument used for determining the position of the apex of a dental root and measuring the thickness of the alveolar bone facing the lip comprising a main body having a mounting portion, a reamer on the mounting portion with an end which may reach the apex of a dental root, an arm disposed alongside of the reamer having a base end rotatably supported on the main body and a free end rotatable toward the reamer, a positioning member on the lower portion of the arm for adjusting the distance between the main body and the arm, and an indicating pin connected to the upper portion of the arm for putting a mark on the gum having a free end alignable with the free end of the reamer. The free end of the indicating pin is aligned with that of the reamer, and the reamer is inserted into the pulp canal of a tooth so that its end may be disposed at the apex of its root. The free end of the indicating pin is pressed into contact with the gum to mark it, and the positioning member is moved so that its end facing the main body abuts the mounting portion to define a fixed distance between the arm and the main body. The arm is turned outwardly, the reamer is drawn out of the pulp canal, and the entire instrument is removed from the mouth.

3 Claims, 5 Drawing Figures

U.S. Patent   Jul. 31, 1984   4,462,802
Fig. 1   Fig. 2   Fig. 3
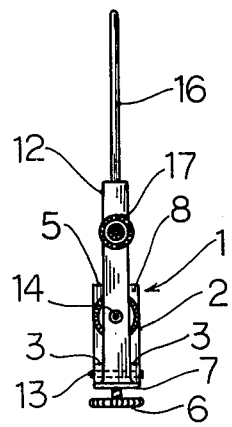
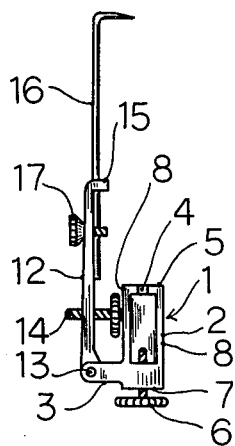
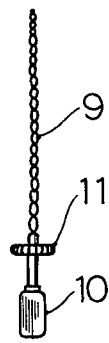
Fig. 4   Fig. 5
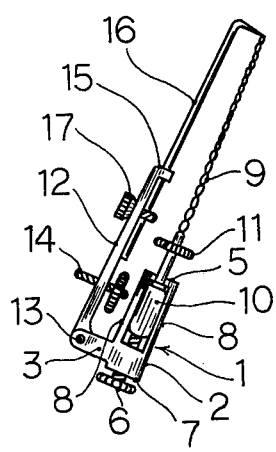
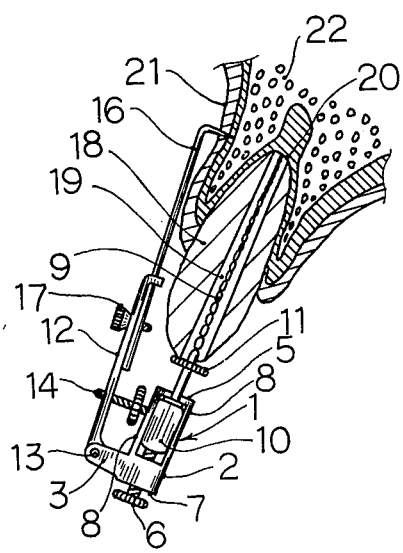

DENTAL ROOT MARKING AND MEASURING INSTRUMENT FOR ENDODONTIC SURGERY

BACKGROUND OF THE INVENTION

1. Field of the Invention

This invention relates to a device for use in the endodontic surgery which is one of the methods for the treatment of diseases of a dental root. More particularly, it is concerned with a dental root marking and measuring instrument for marking the position of a dental root externally and measuring the thickness of a bone.

2. Description of the Prior Art

Endodontic surgery is believed to be a suitable method for the treatment of diseases of a dental root which are difficult to treat through a pulp canal. In order to carry out a surgical operation, however, it is necessary to ascertain the position of a dental root from the exterior. This has hitherto been done by ocular inspection, palpation and intuition of the operator with the aid of an X-ray picture and the findings on the swelling or color of the alveolar bone. If the alveolar bone at the dental root is broken, it is relatively easy to ascertain the position of the dental root. In the event no broken portion of the bone can be easily found with the naked eye, it is sometimes effective to prick strongly with a probe several portions of the alveolar bone which appear to be broken, since the probe can be pierced through any thin bone portion covering the site of a disease. If it is still impossible to locate any broken portion, or if no image of X-ray transmission is observed, it has been usual to dispose a reamer used for measuring the length of a pulp canal along the alveolar bone facing the lip by taking the direction of the dental root into consideration, and assume the position of the dental root from the position of the end of the reamer. In the event even this method is ineffective, an X-ray picture is taken with an X-ray-impermeable object, such as a lead foil or ball, or a small ball of a gold foil, placed in a removed portion of the bone, and the positional relationship between the dental root and the X-ray-impermeable object is examined, whereby the position of the dental root is assumed. All of these methods, however, require a lot of time and labor. It is difficult to determine the position of a dental root correctly, and there is every possibility of making a mistake in locating it. Accordingly, there is every likelihood of the healthy bone being unnecessarily removed, or a normal dental root being damaged.

SUMMARY OF THE INVENTION

It is an object of this invention to provide a dental root marking and measuring instrument which is used in endodontic surgery for diseases of a dental root, and which is used externally for correctly ascertaining the position of a dental root and measuring the thickness of the alveolar bone facing the lip.

It is another object of this invention to provide a dental root marking and measuring instrument which can be used for an endodontic surgical operation without removing the healthy bone unnecessarily, or doing damage to the dental root.

It is still another object of this invention to provide a dental root marking and measuring instrument which is small, light, simple in construction and easy to handle, and can be safely used for endodontic surgery.

This invention provides an instrument essentially comprising a main body having a mounting portion, a reamer having a grip portion mountable on the mounting portion of the main body, and an end adapted to reach a dental root, an arm having a base end rotatably supported on the main body alongside of the reamer, and a free end rotatable toward the reamer, a positioning member provided below the arm for adjusting the distance between the main body and the arm, and an indicating pin having an adjustable end disposed above the arm at the same level of height with the end of the reamer, and adapted to place a mark on the gum.

BRIEF DESCRIPTION OF THE DRAWINGS

FIG. 1 is a side elevational view of an instrument embodying this invention from which the reamer has been removed;

FIG. 2 is a front elevational view of the instrument shown in FIG. 1;

FIG. 3 is a front elevational view of the reamer;

FIG. 4 is a front elevational view of the entire instrument with the reamer mounted on the main body, and the end of the indicating pin aligned with that of the reamer; and FIG. 5 is a view illustrating the mode of use of the instrument in which the reamer is disposed in a pulp canal with its end aligned with the dental root, while the end of the indicating pin is placed in contact with the gum for putting a mark thereon.

DESCRIPTION OF THE PREFERRED EMBODIMENT

Referring to FIGS. 1 and 2 of the drawings, an instrument embodying this invention comprises a main body 1 having a mounting portion 2 of the box-shaped construction which is open on one side, and a pair of bearing portions 3 spaced apart from each other, and projecting laterally from the bottom of the mounting portion 2. The mounting portion 2 comprises a top wall 5 having a slit 4 in its center, a bottom wall 7 provided with a fixing screw 6 in its center, and a sidewall 8. The mounting portion 2 is sufficiently large to receive therein a grip portion 10 formed at the base end of a reamer 9 which is shown in FIG. 3. The reamer 9 is provided intermediate the ends thereof with a slidable rubber stop member 11. An arm 12 has a base end rotatably supported on a shaft 13 held by the bearing portions 3. The arm 12 is disposed alongside of the reamer 9 mounted on the mounting portion 2, and has a free end rotatable about its base end toward the reamer 9. The arm 12 is provided in its lower portion with a positioning member 14 which is movable to and away from the main body 1. The positioning member 14 may, for example, be an adjust screw. The positioning member 14 has one end facing the sidewall 8 of the main body 1 and movable to and away from the sidewall 8 to thereby adjust the distance between the main body 1 and the arm 12. The arm 12 is formed with a bearing portion 15 at its upper end. An indicating pin 16, which may, for example, be formed from a stainless steel wire, extends slidably through the bearing portion 15. The arm 12 is provided with a clamp screw 17 having a shank formed with a diametrically extending hole. The indicating pin 16 has a lower portion extending through the hole of the clamp screw 17. If the screw 17 is loosened, the indicating pin 16 is vertically slidable along the arm 12. If the indicating pin 16 is brought to a predetermined position, the screw 17 can be tightened to hold the pin 16 in that position. The pin 16 has a free or upper end so bent that it may be conveniently aligned with the end of the reamer 9 and placed in contact with the gum for putting a mark thereon.

When the instrument is put in use, the grip portion 10 of the reamer 9 is fitted in the mounting portion 2 of the main body 1, and the clamp screw 6 is tightened to fix the reamer 9 to the main body 1. Then, the indicating pin 16 is slid so that its end may be aligned with that of the reamer 9, and the clamp screw 17 is tightened to secure the pin 16 to the arm 12. A spring means may be used instead of the clamp screw 6 to secure the reamer 9. The length of the pulp canal between a reference point on the crown of the tooth to be operated and its root is measured by a customary method beforehand. The stop member 11 is moved so that the distance between the end of the reamer 9 and the stop member 11 may be equal to the length of the pulp canal. Then, the reamer 9 is inserted into the pulp canal 19 of the tooth 18 to be treated, as shown in FIG. 5. The tooth 18 is given the necessary treatment, including expansion and formation of the pulp canal, before the reamer 9 is inserted therein. If the reamer 9 is inserted until the stop member 11 abuts on the crown of the tooth 18, its end is disposed at the root 20 of the tooth 18 as shown in FIG. 5. If the arm 12 is rotated about the shaft 13 toward the reamer 9, the hooked end of the indicating pin 16 is pressed into contact with the gum 21 or the alveolar bone 22, and puts a mark thereon.

Then, while the indicating pin 16 is kept in that position, the positioning member 14 is moved to the right in FIG. 5 until its end abuts on the sidewall 8 of the main body 1. Then, the pin 16 is moved away from the gum or alveolar bone, and the instrument is removed from the mouth. The pin 16 is moved toward the reamer 9 again until the end of the positioning member 14 abuts on the sidewall 8 of the main body 1, and if the distance between the ends of the reamer 9 and the indicating pin 16 is measured, it is possible to determine the thickness of the alveolar bone 22 facing the lip.

As is obvious from the foregoing description, this invention makes it possible to determine the position of a dental root and the thickness of the alveolar bone facing the lip correctly to thereby enable the formation of an artificial fistula exactly in the center of an affected part around the dental root, and endodontic surgery with a high degree of safety without removing any healthy bone unnecessary, or doing damage to the dental root. The instrument of this invention is small, light, simple in construction and easy to handle. The instrument of this invention is also useful for other operations, such as apicocurettage and apicoectomy. The reamer 9 may be replaced by a graduated reamer wire which provides a reading of the length of a pulp canal. Although in the embodiment hereinbefore described the clamp screw is used to secure the reamer to the main body, it is equally possible to provide the main body with an internally threaded mounting portion and the reamer with an externally threaded grip portion, and connect the reamer threadedly into the main body.

What is claimed is:

1. A dental root marking and measuring instrument for use in endodontic surgery, comprising:
    (a) a main body;
    (b) a reamer;
    (c) a reamer mounting portion provided in said main body, said reamer having a grip portion mounted on said reamer mounting portion so that it may have an end reaching the apex of a dental root;
    (d) an arm disposed alongside of said reamer, and having a base end rotatably supported on said main body and a free end which is rotatable toward said reamer;
    (e) a positioning member provided in the lower portion of said arm for adjusting the distance between said main body and said arm; and
    (f) an indicating pin connected to the upper portion of said arm, and having a free end which is alignable with said end of said reamer, said pin being adapted to put a mark on the gum.

2. An instrument as set forth in claim 1, further including means provided on said mounting portion for securing said reamer thereto.

3. An instrument as set forth in claim 1, wherein said positioning member is a screw.

* * * * *